United States Patent
Gatzemeyer et al.

(10) Patent No.: US 8,075,315 B2
(45) Date of Patent: Dec. 13, 2011

(54) ORAL CARE IMPLEMENT HAVING USER-INTERACTIVE DISPLAY

(75) Inventors: John J. Gatzemeyer, Hillsborough, NJ (US); Eduardo J. Jimenez, Manalapan, NJ (US); Robert Riebe, Minneapolis, MN (US); Evan Ward, Chicago, IL (US); Paul Fair, Denver, CO (US); James E. Michaels, Lombard, IL (US); Kevin Connor, Jackson, NJ (US)

(73) Assignee: Colgate-Palmolive Company, New York, NY (US)

( * ) Notice: Subject to any disclaimer, the term of this patent is extended or adjusted under 35 U.S.C. 154(b) by 797 days.

(21) Appl. No.: 11/610,248

(22) Filed: Dec. 13, 2006

(65) Prior Publication Data

US 2008/0141476 A1  Jun. 19, 2008

(51) Int. Cl.
*G09B 19/00* (2006.01)
*A63F 13/00* (2006.01)
*A46B 15/00* (2006.01)

(52) U.S. Cl. ........ 434/238; 434/118; 434/236; 434/308; 463/1; 15/105

(58) Field of Classification Search .................. 434/238, 434/118, 236, 208; 463/1; 15/105
See application file for complete search history.

(56) References Cited

U.S. PATENT DOCUMENTS

| | | | |
|---|---|---|---|
| 4,207,087 A * | 6/1980 | Morrison et al. | 463/9 |
| 5,232,370 A * | 8/1993 | Hoye | 434/263 |
| 5,673,451 A | 10/1997 | Moore et al. | |
| 5,810,601 A | 9/1998 | Williams | |
| 5,864,288 A | 1/1999 | Hogan | |
| 5,875,796 A | 3/1999 | Silver-Isenstadt et al. | |
| 5,924,159 A | 7/1999 | Haitin | |
| 5,930,858 A | 8/1999 | Jung | |
| 5,943,723 A * | 8/1999 | Hilfinger et al. | 15/22.1 |
| 5,944,531 A * | 8/1999 | Foley et al. | 434/263 |
| 6,154,912 A | 12/2000 | Li | |
| 6,199,239 B1 | 3/2001 | Dickerson | |
| 6,202,242 B1 | 3/2001 | Salmon et al. | |
| 6,389,633 B1 * | 5/2002 | Rosen | 15/105 |
| 6,442,787 B2 | 9/2002 | Hohlbein | |
| 6,461,238 B1 * | 10/2002 | Rehkemper et al. | 463/6 |
| 6,536,068 B1 * | 3/2003 | Yang et al. | 15/105 |
| 6,611,780 B2 * | 8/2003 | Lundell et al. | 702/122 |
| 6,731,213 B1 * | 5/2004 | Smith | 340/573.1 |
| 6,754,928 B1 * | 6/2004 | Rosen | 15/105 |

(Continued)

FOREIGN PATENT DOCUMENTS

CA  2 232 528 A1  9/1999

(Continued)

OTHER PUBLICATIONS

International Search Report of PCT/US2007/087134, Mar. 25, 2008.

(Continued)

*Primary Examiner* — Kang Hu
(74) *Attorney, Agent, or Firm* — Judy W. Chung

(57) ABSTRACT

An oral care implement has an interactive display that displays images representing oral care regions of the mouth. The user can interact with the display by playing a game, which can relate to oral care. An oral care implement has a plurality of lighted segments that can be sequentially illuminated to indicate a recommended brushing sequence. The lighted segments can be shaped and/or labeled to indicate particular oral care regions of the mouth.

11 Claims, 13 Drawing Sheets

U.S. PATENT DOCUMENTS

| | | | |
|---|---|---|---|
| 6,802,097 B2 | 10/2004 | Hafliger et al. | |
| 6,850,167 B2 * | 2/2005 | Rosen | 340/689 |
| 6,954,961 B2 * | 10/2005 | Ferber et al. | 15/22.1 |
| 7,003,839 B2 | 2/2006 | Hafliger et al. | |
| 7,448,109 B2 | 11/2008 | Brewer et al. | |
| 7,976,388 B2 * | 7/2011 | Park et al. | 463/37 |
| 2001/0034917 A1 | 11/2001 | DuCey | |
| 2001/0050507 A1 | 12/2001 | Boucherie | |
| 2003/0017874 A1 * | 1/2003 | Jianfei et al. | 463/46 |
| 2003/0063011 A1 | 4/2003 | Rosen | |
| 2003/0115694 A1 | 6/2003 | Pace | |
| 2003/0205492 A1 | 11/2003 | Ferber et al. | |
| 2004/0134000 A1 | 7/2004 | Hilfinger et al. | |
| 2005/0091769 A1 | 5/2005 | Jimenez et al. | |
| 2005/0229345 A1 * | 10/2005 | Rouse et al. | 15/105 |
| 2006/0037158 A1 * | 2/2006 | Foley et al. | 15/105 |
| 2006/0040246 A1 * | 2/2006 | Ding et al. | 434/263 |
| 2006/0117508 A1 | 6/2006 | Hohlbein | |
| 2006/0257822 A1 * | 11/2006 | Ghosh et al. | 433/215 |
| 2006/0272113 A1 | 12/2006 | Cato et al. | |
| 2007/0094822 A1 | 5/2007 | Gatzerneyer et al. | |
| 2007/0136964 A1 * | 6/2007 | Dawley | 15/22.1 |
| 2007/0270221 A1 | 11/2007 | Park et al. | |
| 2008/0109973 A1 * | 5/2008 | Farrell et al. | 15/4 |
| 2009/0143914 A1 | 6/2009 | Cook et al. | |

FOREIGN PATENT DOCUMENTS

| | | |
|---|---|---|
| CN | 2299526 | 12/1998 |
| CN | 1416759 | 5/2003 |
| CN | 2633244 | 8/2004 |
| CN | 2685937 | 3/2005 |
| DE | 3935554 | 8/1991 |
| DE | 4029770 | 3/1992 |
| DE | 19506129 | 8/1996 |
| DE | 299 15 858 U1 | 9/1999 |
| DE | 10001502 | 3/2001 |
| DE | 100 26 513 A1 | 5/2001 |
| DE | 10045353 | 3/2002 |
| DE | 10120090 | 8/2002 |
| DE | 101 54 946 A1 | 5/2003 |
| DE | 10247698 | 4/2004 |
| DE | 102006005205 A1 | 9/2006 |
| FR | 2544602 | 10/1984 |
| JP | 8-19427 A | 1/1996 |
| JP | 2003310644 | 11/2003 |
| JP | 2002369718 | 12/2005 |
| RU | 2098993 | 12/1997 |
| RU | 2174381 | 10/2011 |
| WO | 2006/065159 A2 | 6/2006 |
| WO | WO 2006/137648 | 12/2006 |
| WO | WO 2007/072430 | 6/2007 |
| WO | WO 2007/097886 | 8/2007 |

OTHER PUBLICATIONS

Examiner's First Report from the Patent Office of Australia for corresponding Australian Patent Application No. 2008216204 dated Sep. 23, 2010.

Examination Report from the National Office of Intellectual Property of Vietnam for corresponding Vietnamese Patent Application No. 1-2009-01946 dated Mar. 23, 2011.

International Search Report in International Application No. PCT/US08/05390O mailed Jul. 3, 2008.

Search Report from the intellectual Property Office of Taiwan for corresponding Taiwan Patent Application No. 097105282 dated Jan. 26, 2011.

* cited by examiner

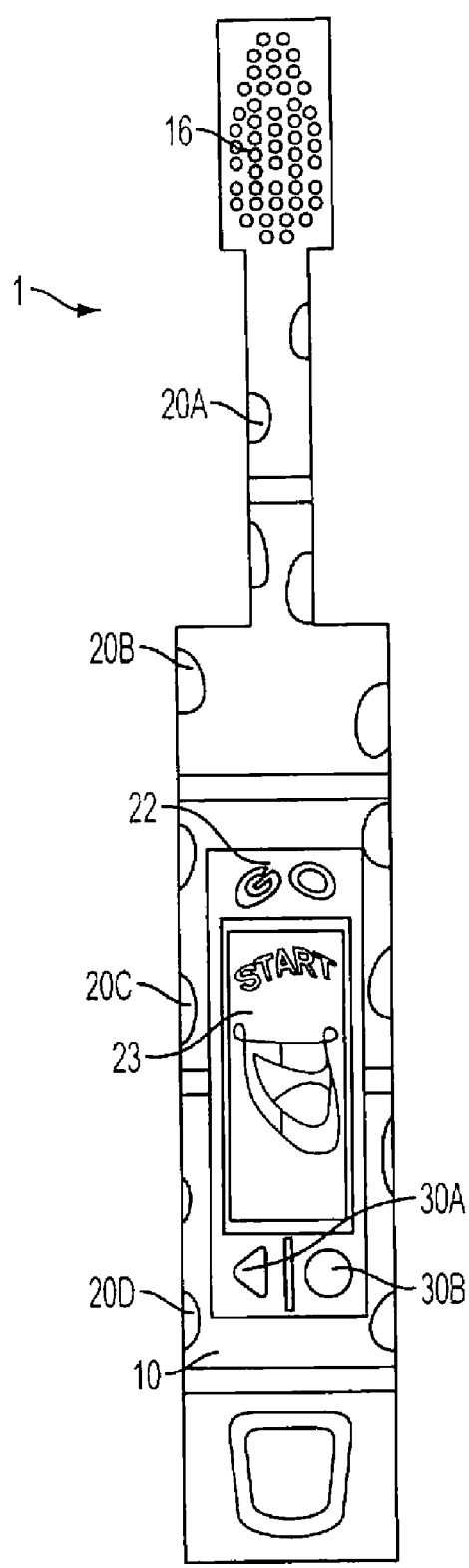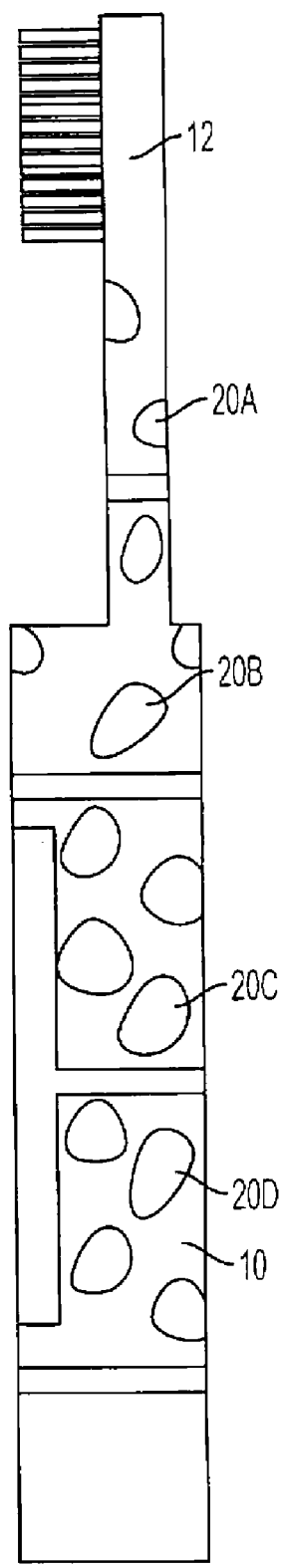
FIG. 2A                    FIG. 2B

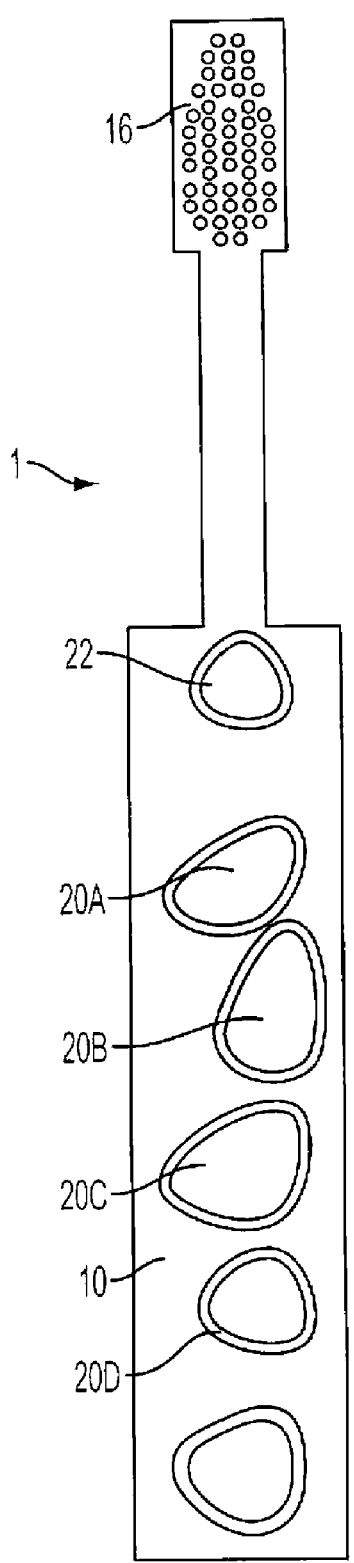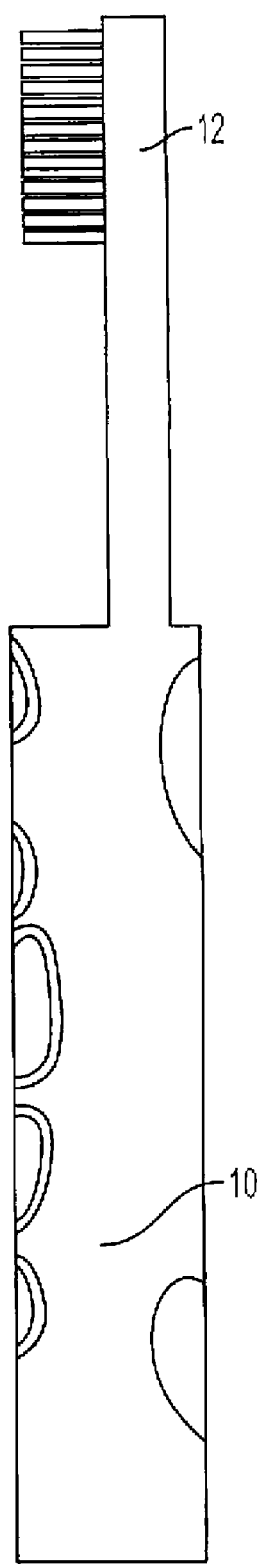
FIG. 3A                    FIG. 3B

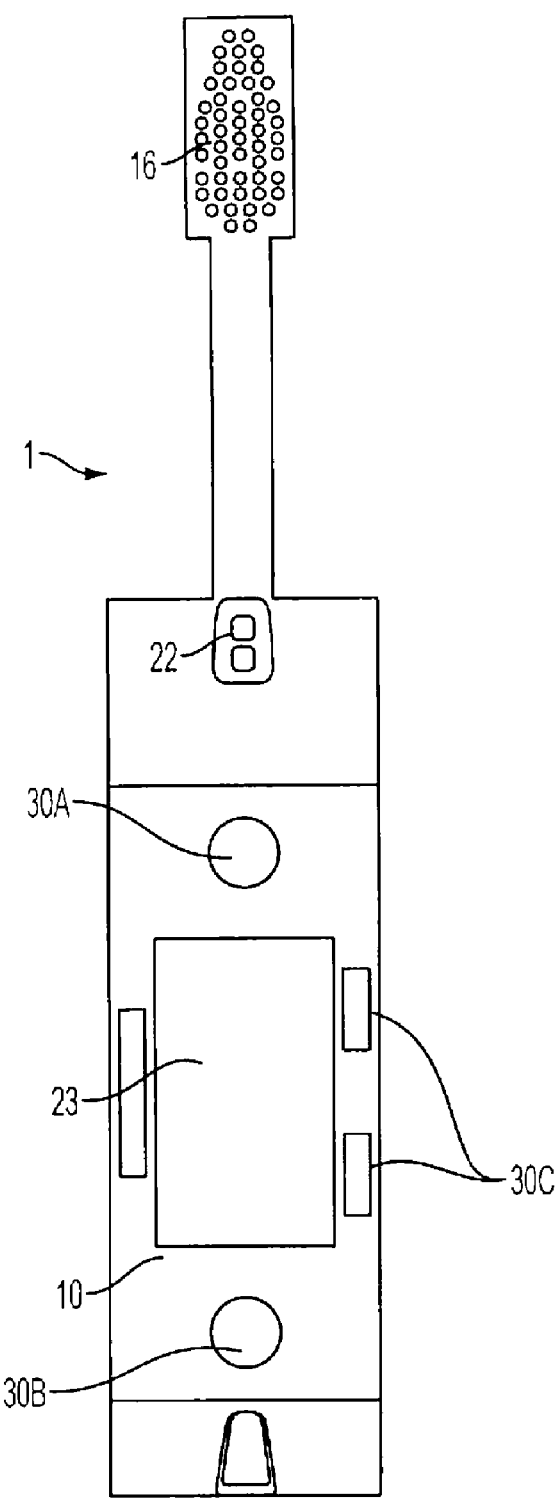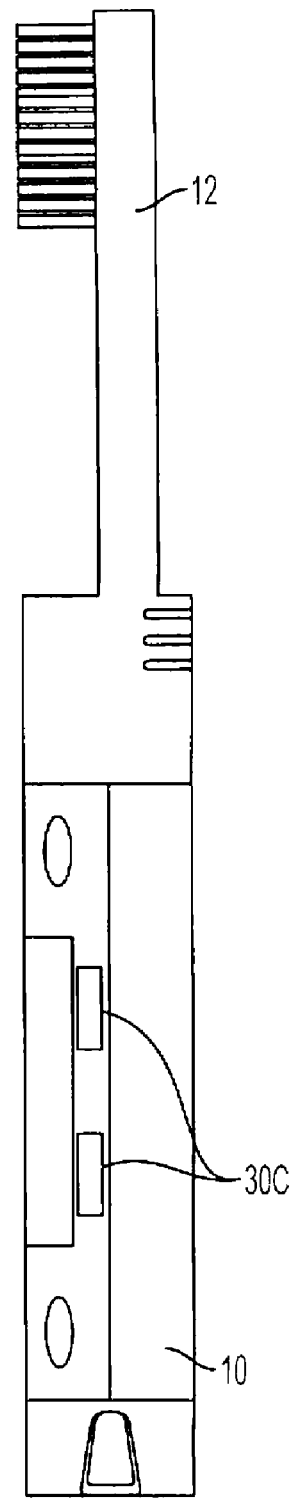
FIG. 6A
FIG. 6B

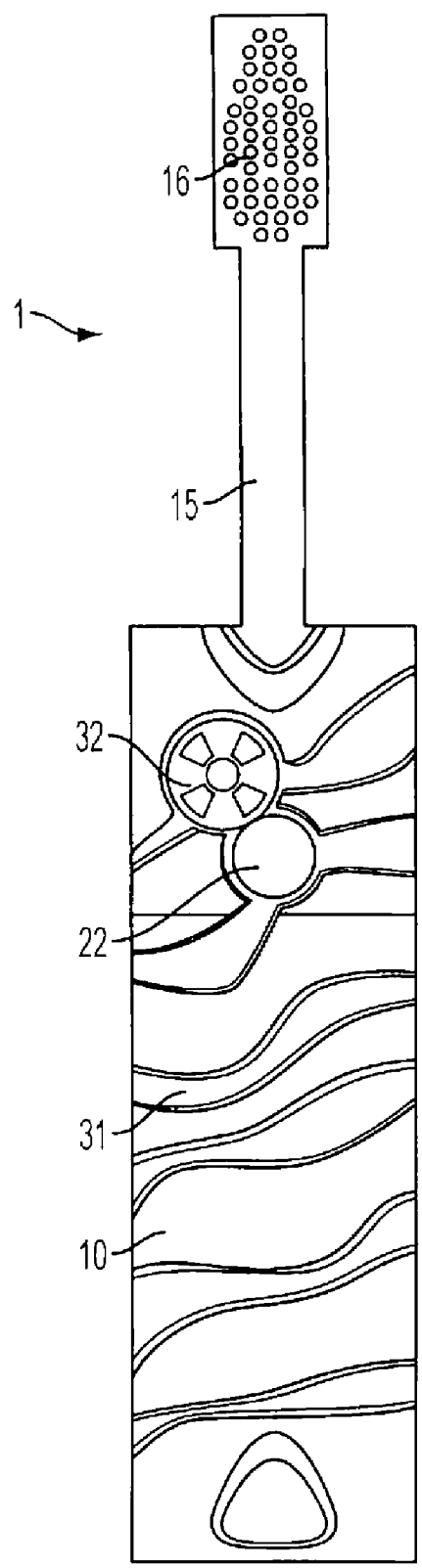
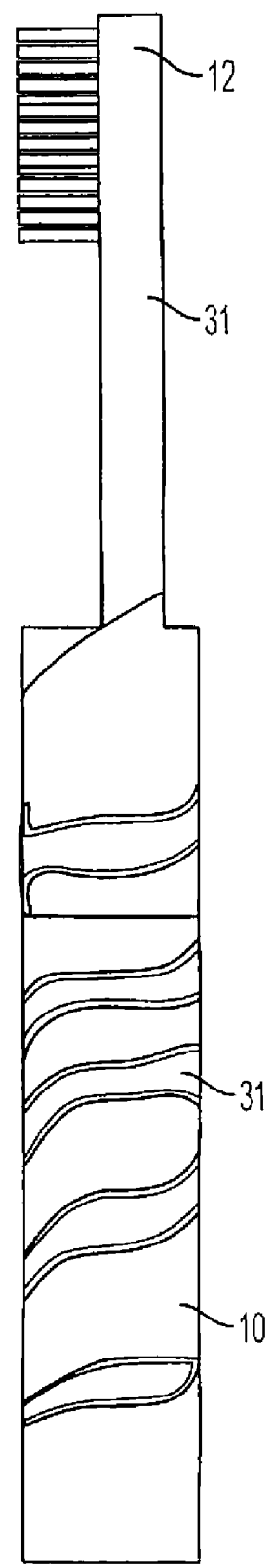
FIG. 8A
FIG. 8B

ORAL CARE IMPLEMENT HAVING USER-INTERACTIVE DISPLAY

FIELD OF INVENTION

The present invention pertains to an oral care implement that provides an entertaining and/or educational interactive competition for a user.

BACKGROUND OF THE INVENTION

Dentists generally recommend that an individual brush their teeth for a minimum interval per cleaning, such as two minutes. Despite such recommendations, many individuals, especially young children, do not regularly brush their teeth for the recommended minimum interval. Such habits often can be attributed to the individual regarding tooth brushing as a mundane duty with few pleasurable aspects.

A toothbrush providing brushing behavior reinforcement is described in U.S. Pat. No. 6,389,633 to Rosen. A motion sensing means is used to monitor the brushing action of the user. When the logic requirements of motion sensing are complete, the logic means directs a digital output display means to output to a small LCD screen or speaker a visual and/or audible indication to the user, such as in the form of a rudimentary game or congratulatory message.

There remains a need for alternative techniques for promoting oral hygiene, and particularly for providing an incentive to users to brush their teeth for at least a minimum recommended brushing interval.

BRIEF SUMMARY OF THE INVENTION

The present invention pertains to an oral care implement, such as a toothbrush, that provides an entertaining and/or educational interactive competition for the user to promote improved oral hygiene.

The present invention provides an entertaining and/or educational environment in which a user/player brushes their teeth and interacts with a computer implemented game on a toothbrush. In one embodiment, an oral care implement provides for a synergistic combination of education and entertainment games pertaining to oral care hygiene. An individual is provided with an interactive reward in which virtual elements performing the educational functions form the basis of an interactive computer game for the user/player. Hence, an educational game directed to oral care can be more entertaining than simple instructions.

According to one embodiment, an oral care implement includes a plurality of lighted segments for indicating two or more oral care regions of the mouth. The oral care implement includes a computer processor for causing the segments to be sequentially lighted for prescribed intervals. The segments can be used to instruct a user to brush in a particular oral care region during the prescribed interval.

In another embodiment, an oral care implement includes a display screen for displaying images associated with oral care regions of the mouth, and an input device configured for interacting with the images. The images can be sequentially displayed to instruct the user to brush in particular oral care regions during sequential intervals. The user can interact with the images by playing a game or the like.

In another embodiment, an oral care implement comprises a computer processor, a display, and a memory for storing instructions. When executed by the processor, the memory causes the oral care implement to sequentially display graphical objects at prescribed intervals, and enable user interaction with the graphical objects. The user can interact with the graphical objects by playing a game or the like.

In yet another embodiment, an oral care implement comprises a display for displaying graphical objects associated with oral care. The graphical objects collectively define a computer implemented process for oral care gaming. The oral care implement has an input device to allow a user to interact with the computer implemented process.

In one embodiment, an oral care implement comprises a microprocessor, a display, and a digital memory for storing instructions. When executed by the microprocessor, the memory causes the oral care implement to sequentially display text at prescribed intervals and display graphical objects. The memory also enables user interaction with the graphical objects.

BRIEF DESCRIPTION OF THE DRAWINGS

The features, and advantages of the invention will be apparent from the following more detailed description of certain embodiments of the invention and as illustrated in the accompanying drawings in which:

FIG. 2A is a front view of a toothbrush according to another embodiment of the invention; FIG. 2B is a side view of the toothbrush of FIG. 2A;

FIG. 3A is a front view of a toothbrush according to another embodiment of the invention; FIG. 3B is a side view of the toothbrush of FIG. 3A;

FIG. 6A is a front view of a toothbrush according to another embodiment of the invention; FIG. 6B is a side view of the toothbrush of FIG. 6A.

FIG. 8A is a front view of a toothbrush according to another embodiment of the invention; FIG. 8B is a side view of the toothbrush of FIG. 8A.

DETAILED DESCRIPTION OF THE INVENTION

Figure 1A:
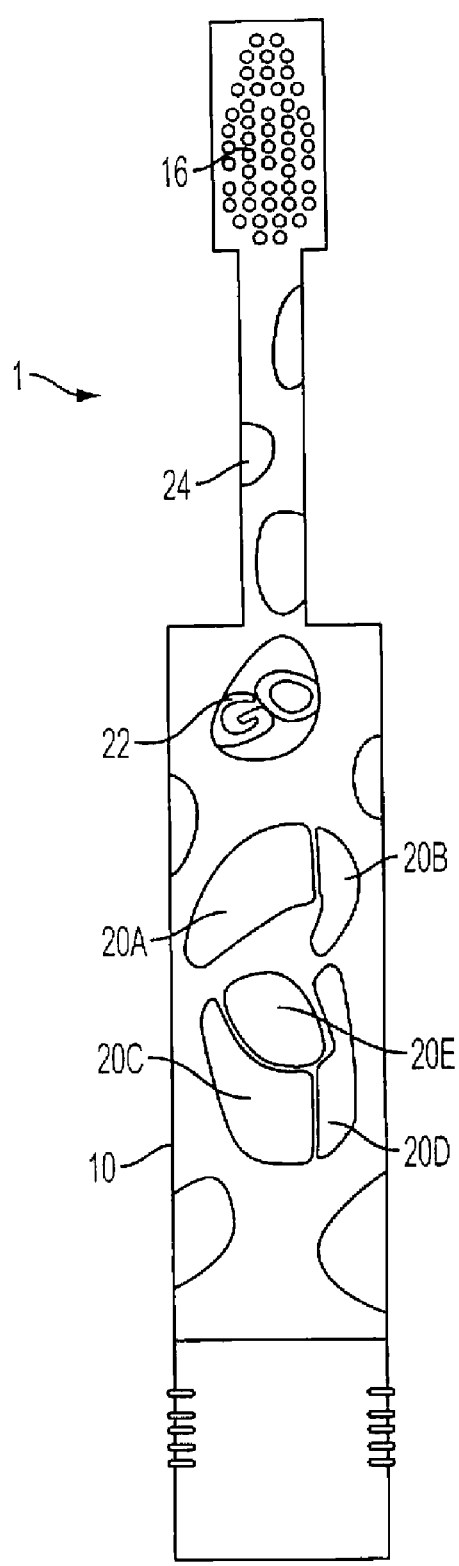
FIG. 1A is a front view of a toothbrush according to one embodiment of the invention.
Figure 1B:
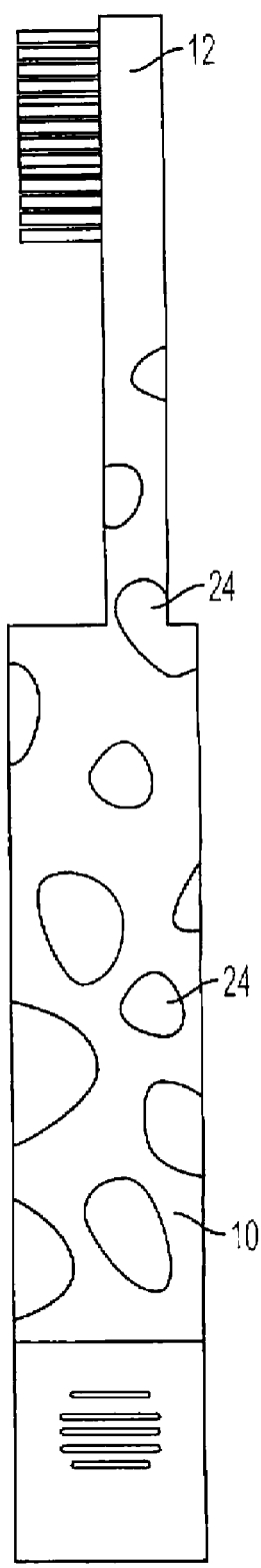
FIG. 1B is a side view of the toothbrush of FIG. 1A.

FIGS. 1A and 1B illustrate a toothbrush 1 having a handle 10 and a head 12 containing tooth cleaning elements, such as bristles 16 and/or elastomeric cleaning elements (not shown). Any bristle configuration and any handle configuration can be used, and the present invention should not be regarded as being limited to any particular configuration. Toothbrushes described and shown in other embodiments below may share these features and such description will not be repeated, with like reference numerals corresponding to like elements. The toothbrush may be manual or powered, e.g., battery-powered.

In the embodiment shown in FIGS. 1A and 1B, the toothbrush 1 includes a plurality of lighted segments 20A-20E, which together resemble tooth quadrants and a tongue. A button 22 is provided to enable a user to activate the functionality of the toothbrush, as described below. The toothbrush 1 optionally may include a plurality of additional lighted areas 24 at various locations of the handle 10. The lighted areas 24 may be uniformly sized and spaced or, as shown in FIGS. 1A and 1B, may be differently sized and/or spaced if desired. The button 22 may be similar in appearance to the lighted areas 24 and optionally may be lighted. Alternatively, some or all of areas 24 may be decorative only instead of being lighted.

The lighted segments 20A-20E may together resemble an open mouth, with four generally quarter-circle shaped portions 20A-20D resembling groups of teeth surrounding a generally teardrop shaped portion 20E resembling a tongue, as illustrated in FIG. 1A. An internal memory can be configured so that when a user depresses button 22, one or more of the segments is illuminated to instruct the user to brush in a particular brushing zone for a prescribed interval of time. Additional segments thereafter can be sequentially illuminated to instruct the user to brush in additional brushing zones. A suitable interval of time can be selected for each zone, e.g., about 30 seconds. The interval for a zone can be the same or different than the interval for other zone(s).

For example, segments 20B and 20D can be illuminated during a first 30-second interval to instruct the user to brush the outside surfaces of the top and bottom teeth, including the front and back teeth. At the conclusion of the first interval, a second 30-second interval begins during which segment 20C may be illuminated to instruct the user to brush the upper molars. At the conclusion of the second interval, segment 20A may be illuminated during a third 30-second interval to instruct the user to brush the lower molars. During a fourth 30-second interval, segment 20E may be illuminated to instruct the user to brush the tongue and the surfaces behind the teeth. A four-interval brushing cycle is described merely as exemplary and other values for the time duration of the intervals are possible. If desired, a different number of intervals may be chosen, such as two (e.g., upper teeth/lower teeth), three (e.g., front teeth/upper teeth/lower teeth), five (e.g., outside teeth/upper molars/lower molars/back surfaces/tongue), and so on.

After the user has completed brushing in the prescribed brushing zones, some or all of the lighted areas 20A-20E, 22, and 24 can be illuminated, e.g., flashed in a random sequence. The memory can be programmed to cause such lighting for a prescribed interval of time, e.g., 15-20 seconds, as a signal that the user has completed the recommended brushing program. A young child will be encouraged to complete the entire brushing program to receive the reward of this "light show."

FIGS. 2A and 2B illustrate another embodiment in which the toothbrush is divided into a plurality of sections each having a plurality of lighted areas 20A, 20B, 20C, and 20D. A display screen 23 is provided for displaying graphical objects. For example, when button 22 is depressed, the display screen can display "start" and a graphical object representing teeth and a tongue, with a portion of the teeth shaded as an instruction to brush the outside surfaces of the upper and lower teeth for a prescribed interval. The display screen 23 also may display a timer that indicates the amount of time remaining in the interval, e.g., in seconds. During the interval, lighted areas 20D in one of the sections are caused to blink as an additional indicator of the current brushing zone. At the conclusion of the interval, a graphical object representing a subsequent brushing zone, e.g., front teeth, can be displayed while lighted areas 20C in another section are caused to blink. This procedure can be repeated for additional brushing zones, e.g., upper molars, lower molars, etc., by displaying a representative object on the display screen 23 and illuminating the lighted areas 20B, 20A, etc. in one of the sections.

At the conclusion of the prescribed brushing intervals, all of the lighted areas 20A-20D can be caused to blink, if desired, as a signal that brushing has been completed. The display screen 23 can then be caused to visually present a game, with which the user can interact via controls 30A and 30B. As discussed more fully below, the game can utilize some or all of the objects displayed during brushing. For example, the user may control a "gunship" that fires shots to remove plaque from teeth. The controls 30A and 30B can be used to move the gunship left and right and to fire shots, for example. Furthermore, audio may be provided to enhance the gameplay.

As a variation of the "gunship" game, the display screen 23 can be configured so that simulated plaque pieces descend from the top of the screen (e.g., which can be oriented vertically) at random lateral positions. Rectangles representing teeth are displayed across the bottom of the screen. The player controls lateral movement of a toothbrush positioned above the teeth. The object of the game is to position the toothbrush below a descending plaque piece to intercept it before it falls onto a tooth. When a plaque piece is successfully intercepted, it disappears and the player then attempts to intercept subsequent plaque pieces. The velocity and/or frequency of the falling plaque pieces can be made to increase as the game progresses to make the game more challenging the longer it is played. The game can end, for example, when a predetermined number of plaque pieces fall onto a tooth.

FIGS. 3A and 3B illustrate an alternative embodiment in which lighted buttons 20A, 20B, 20C, and 20D are provided as indicators of a plurality of brushing zones, e.g., front teeth, upper molars, lower molars, and tongue. After button 22 is depressed, the lighted buttons 20A, 20B, 20C, and 20D are successively caused to be illuminated for respective brushing intervals, e.g., 30-second intervals. At the conclusion of the brushing intervals, the lighted buttons 20A, 20B, 20C, and 20D can be used for a memory game. For example, two or more of the lighted buttons 20A, 20B, 20C, and 20D can be blinked in succession. The object of the game is for the user to repeat the lighting sequence. If the player correctly repeats the lighting sequence, an audible message can be played, such as "good job," and a more complex (e.g., longer sequence) of buttons 20A, 20B, 20C, and 20D can be blinked for the next round. If the player does not correctly repeat a lighting sequence, the player may be given an additional opportunity to repeat the same sequence. Optionally, an incorrectly entered sequence can be indicated in some manner, such as by flashing all of the lighted buttons 20A, 20B, 20C, and 20D together, before the sequence is repeated. Optionally, the game can end after one incorrect sequence (or alternatively two or more consecutive incorrect sequences) are entered.

Figure 4A:
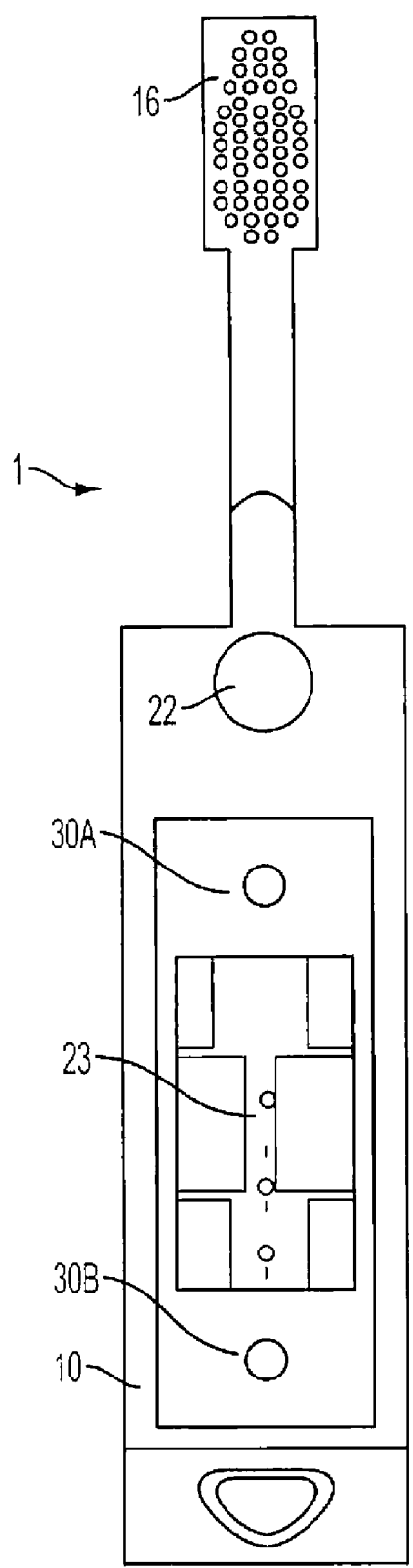
FIG. 4A is a front view of a toothbrush according to another embodiment of the invention.
Figure 4B:
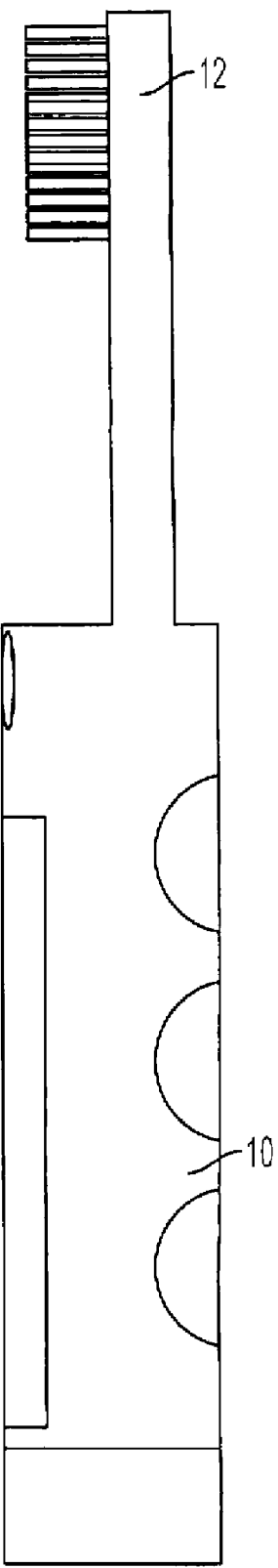
FIG. 4B is a side view of the toothbrush of FIG. 4A.

FIGS. 4A and 4B illustrate another embodiment of a toothbrush 1 having a display screen 23 and game controllers 30A, 30B. The display screen includes six generally rectangular shaped areas representative of tooth sections. Brushing intervals can be indicated by illuminating two or more of the rectangular shaped areas at a time, e.g., to indicate front teeth, upper molars, lower molars, etc. When the user depresses button 22, the display screen 23 displays an indication of the current brushing zone for a prescribed interval. At the conclusion of the brushing intervals, the display screen 23 can present a game, which can include the same graphical objects used during the brushing intervals. For example, the player can control a simulated laser gun/battling character that shoots plaque off of teeth. In this way, incorporating educational oral care concepts into virtual graphical entities (e.g., simulated teeth and plaque) that the player can battle has the effect of making the gameplay more engaging and entertaining to promote good brushing habits.

Figure 5A:
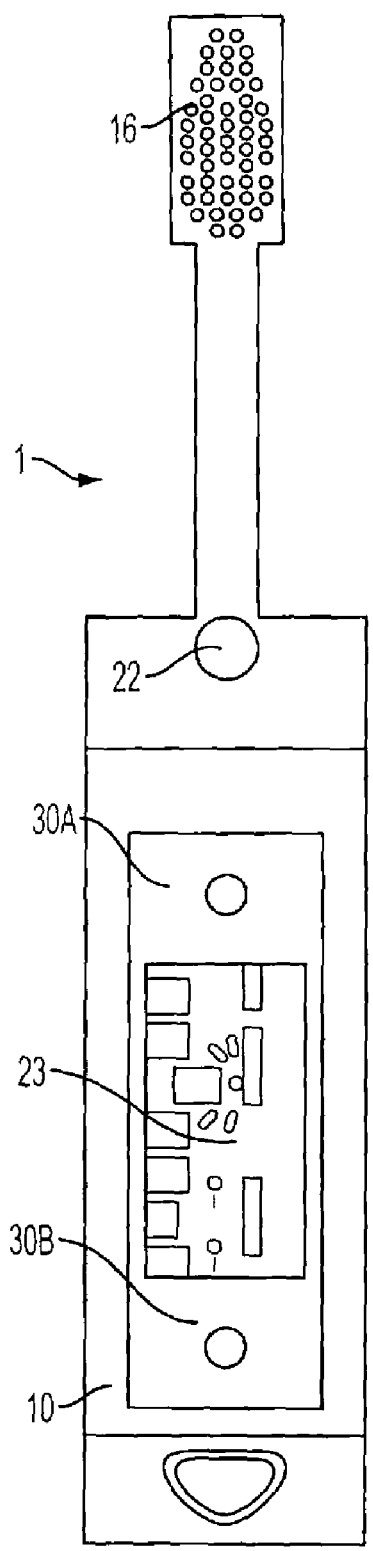
FIG. 5A is a front view of a toothbrush according to yet another embodiment of the invention.
Figure 5B:
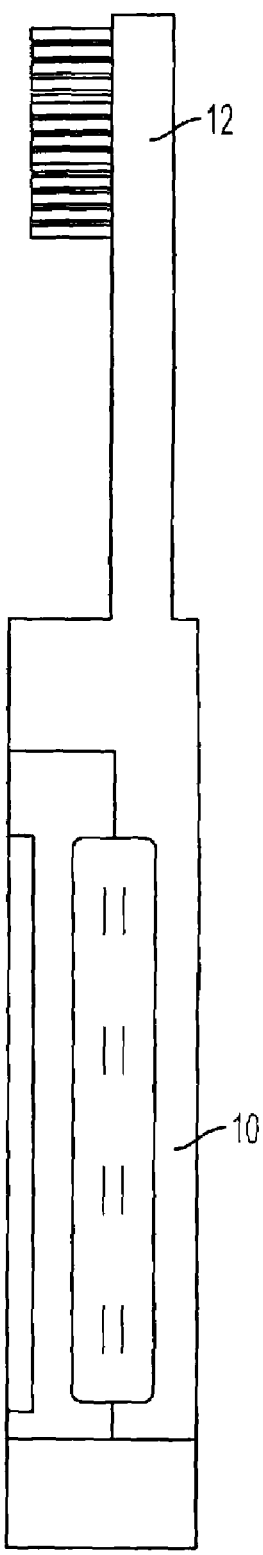
FIG. 5B is a side view of the toothbrush of FIG. 5A.
Figure 5C:
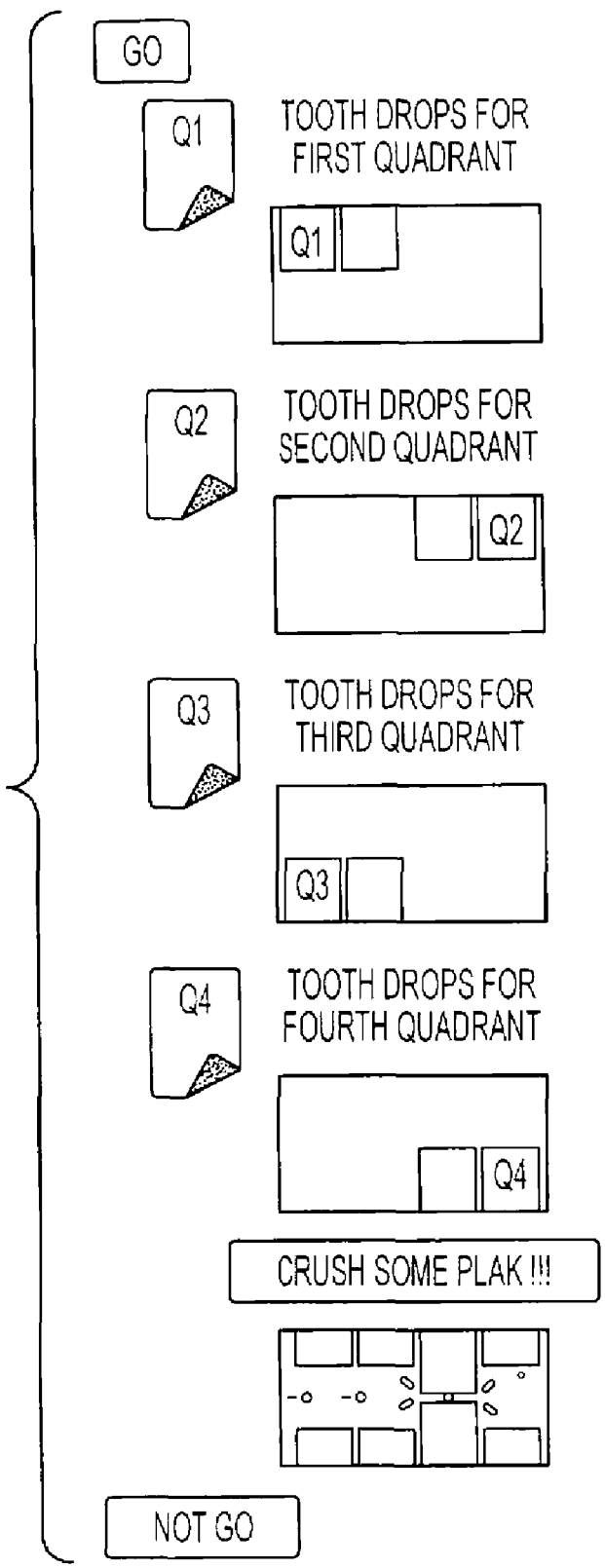
FIG. 5C is a schematic illustration of objects displayed during tooth brushing.

FIGS. 5A and 5B illustrate an alternative embodiment in which the brushing zones are indicated by graphical objects at different locations on the display screen 23. As shown in FIG. 5C, for example, during a first interval two rectangles can be displayed in the upper left corner of the display screen 23 to represent a first brushing zone, e.g., front teeth. Successive intervals are indicated by displaying similar rectangles in the upper right, lower left, and lower right corners of the display screen 23. At the conclusion of brushing, the display screen 23 displays a game, which can include the same graphical objects used during the brushing intervals. For example, the player can select a set of upper and lower "teeth" using one controller 30A, and use another controller 30B to cause the selected "teeth" to converge in an attempt to trap an object (e.g., simulating plaque) therebetween. In this way, incorporating educational oral care concepts into virtual graphical entities that the player can control has the effect of making the gameplay more engaging and entertaining to promote good oral hygiene habits.

Figure 6C:
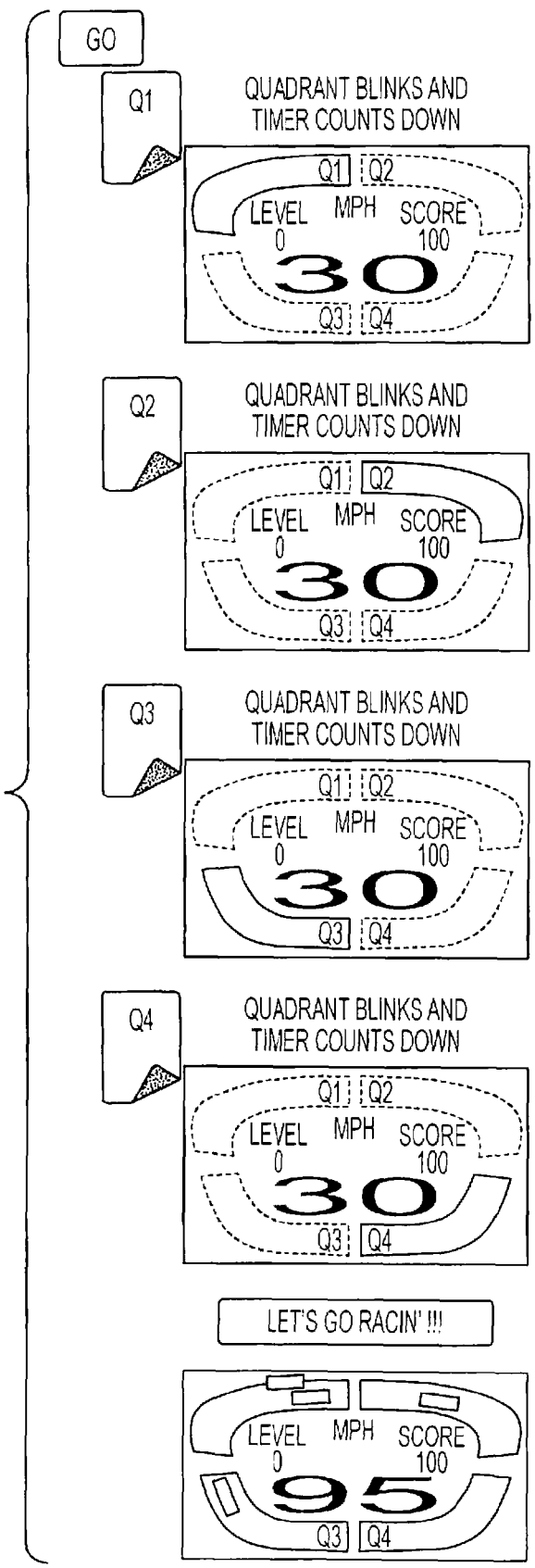
FIG. 6C is a schematic illustration of objects displayed during tooth brushing.

In the embodiment illustrated in FIGS. 6A-6C, a display screen 23 includes four quadrants around its periphery (see FIG. 6C) to indicate four brushing zones. The center portion of the display can be used to display the time (e.g., seconds) remaining in the brushing interval. At the conclusion of brushing, the display can be converted into a game, for example, in which the peripheral quadrants are together used as a racetrack around which cars race. The player can control the motion of the car using controls 30A and 30B. Additional game controls 30C optionally can be provided, or areas 30C optionally can be molded as non-functional decorative detail.

Figure 7A:
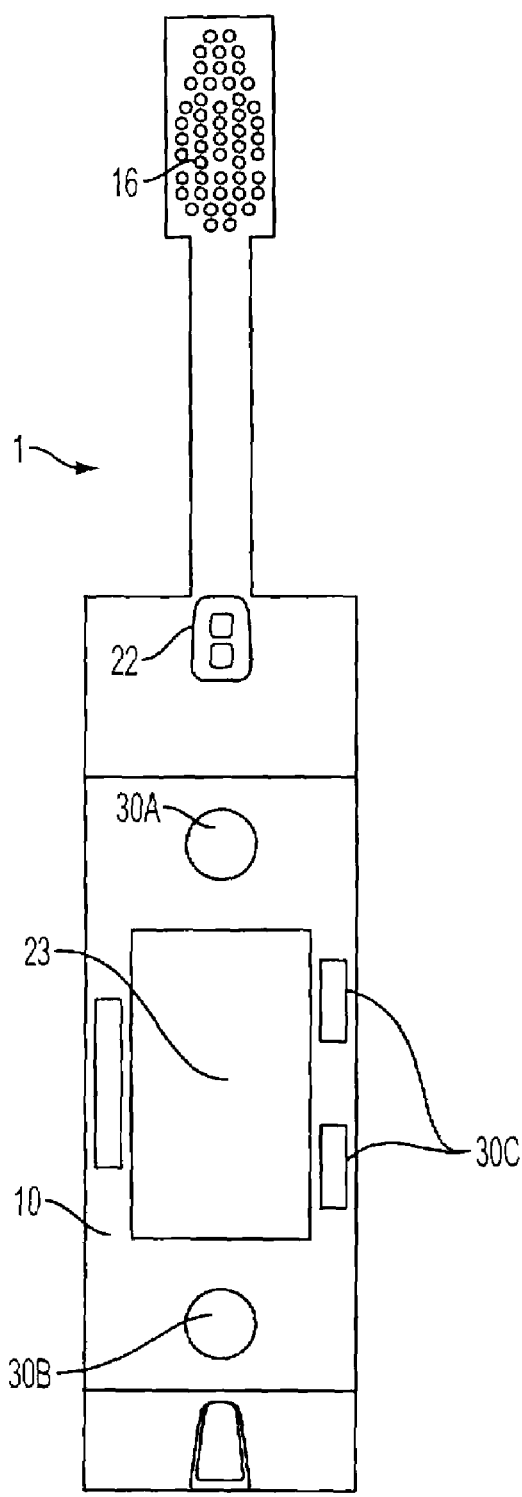
FIG. 7A is a front view of a toothbrush according to yet another embodiment of the invention.
Figure 7B:
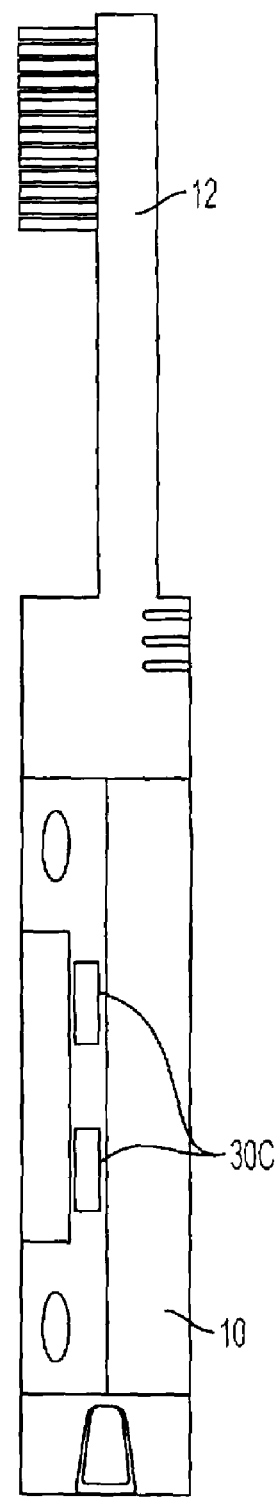
FIG. 7B is a side view of the toothbrush of FIG. 7A.
Figure 7C:
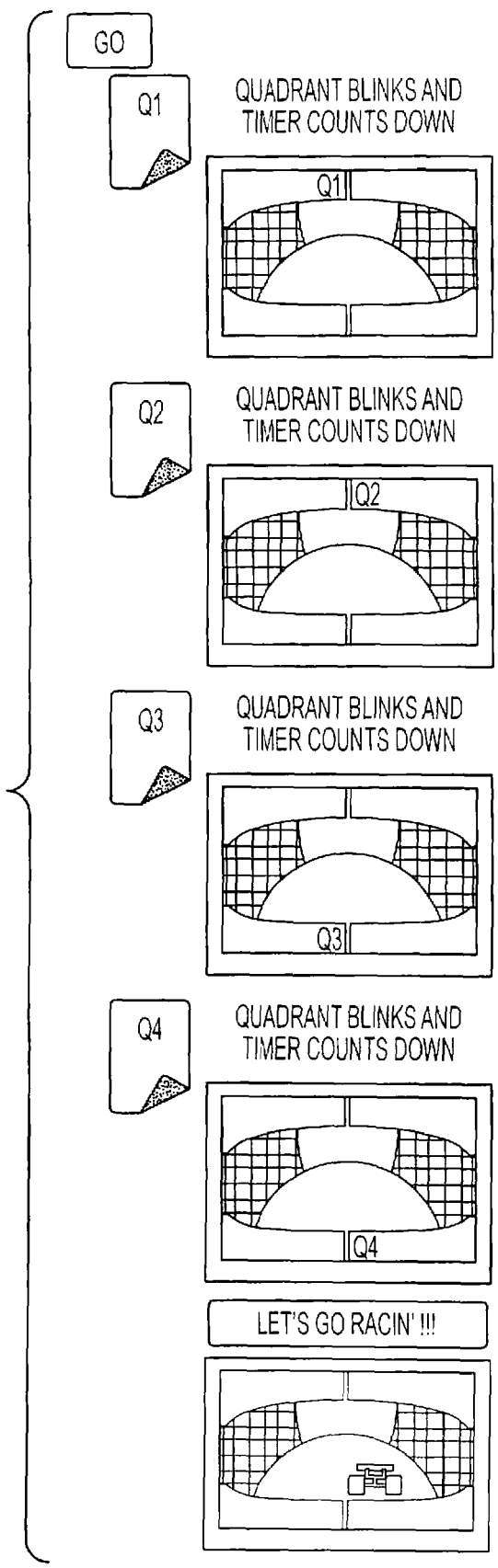
FIG. 7C is a schematic illustration of objects displayed during tooth brushing.

FIGS. 7A-7C illustrate an alternative embodiment in which four peripheral quadrants on the display screen 23 simulate groups of teeth, and a semicircular shaped object representative of a tongue. During brushing, the display screen 23 may display a timer indicating the time remaining in each brushing zone as well as an indicator in the quadrant representative of the current brushing zone. At the conclusion of brushing, the display screen 23 can display a race car, which the player controls via controllers 30A, 30B, and optionally 30C. The game can utilize some or all of the same graphical objects displayed during brushing.

FIGS. 8A and 8B show another embodiment of a toothbrush 1 having a translucent neck portion 15, under which a plurality of different colored light emitting diodes (LEDs) are provided. After the user depresses button 22, successive brushing zones are indicated by illuminating one of the LEDs (e.g., 30 seconds blue, 30 seconds red, 30 seconds green, and then 30 seconds pink). At the conclusion of brushing, the LEDs can be illuminated in a random sequence, for example, to signal that brushing has been completed. Optionally, a speaker 32 may provide voice instructions during the respective intervals (e.g., "start brushing," "brush front teeth," "brush upper molars," etc.). At the conclusion of brushing, the speaker can play music or give a congratulatory message.

Figure 9A:
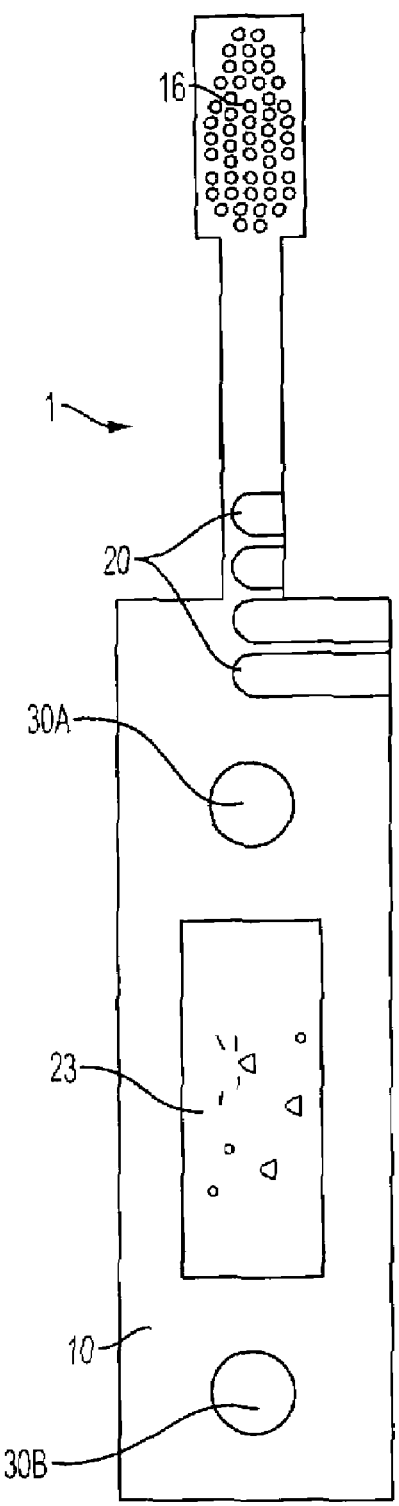
FIG. 9A is a front view of a toothbrush according to another embodiment of the invention.
Figure 9B:
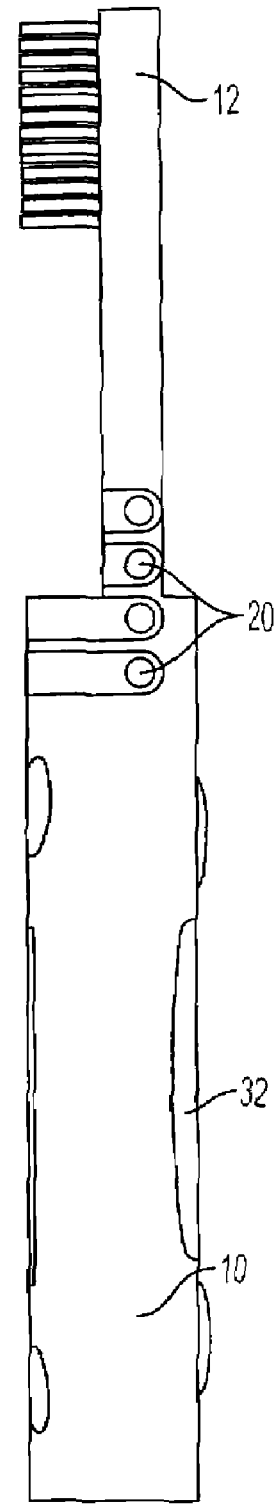
FIG. 9B is a side view of the toothbrush of FIG. 9A.

FIGS. 9A and 9B show an alternative embodiment having a plurality of indicator lights 20 that are illuminated during respective intervals for sequential brushing zones. A display screen 23 can be used to display text for each of the brushing zones (e.g., "front teeth," "upper molars," etc.) during the respective interval. The indicator lights 20 can blink randomly at the conclusion of brushing to signal that brushing has been completed. Following brushing, the display screen 23 can be used to display a game that the user controls via controllers 30A and 30B.

Optionally, the toothbrush 1 may include a motion sensor. A logic circuit can be programmed to shut power off, pause a timer, or take other suitable action in the event the toothbrush is not oscillated in a brushing motion for more than a threshold period of time, e.g., 3-5 seconds. This can help prevent a child from merely watching the light displays or playing the games without actually brushing his or her teeth. In addition, a motion sensor can help preserve battery life by automatically shutting power off when the toothbrush is not in use.

The toothbrush 1 may have a speaker and a suitable audio driver. An audible signal can announce the brushing zone. This may be particularly desirable in embodiments where the visual display(s) are not as easily seen by the user while brushing. The audible signal can be a sound such as beep or chime, which may or may not be distinct for each brushing zone, or may be a voice that announces a brushing zone ("start brushing," "brush front teeth," "brush upper molars," "brush lower molars," "brush tongue," "done," etc.). Optionally, the toothbrush may have mute button to toggle sound on and off.

As described above, the games can utilize the graphic objects or images used during the brushing intervals, e.g., images or objects representing or depicting the mouth, teeth, gums, tongue, etc. Such games can encourage good oral hygiene, such as by having an object of the game is removing plaque from teeth. In addition, having a mouth, teeth, or the like as scenery or background in a game can help draw attention to the user's teeth and need for oral care.

A wide variety of games can be programmed. For example, an "electronic pet" such as a Tamagotchi pet or NeoPet can be programmed. Generally, the game requires the user to "feed" the pet, which enables the pet to evolve into a wide range of characters, depending on how well the user cares for the pet. If the pet is not adequately "nourished," it may lose strength and its evolution into the characters can be inhibited.

Figure 10:
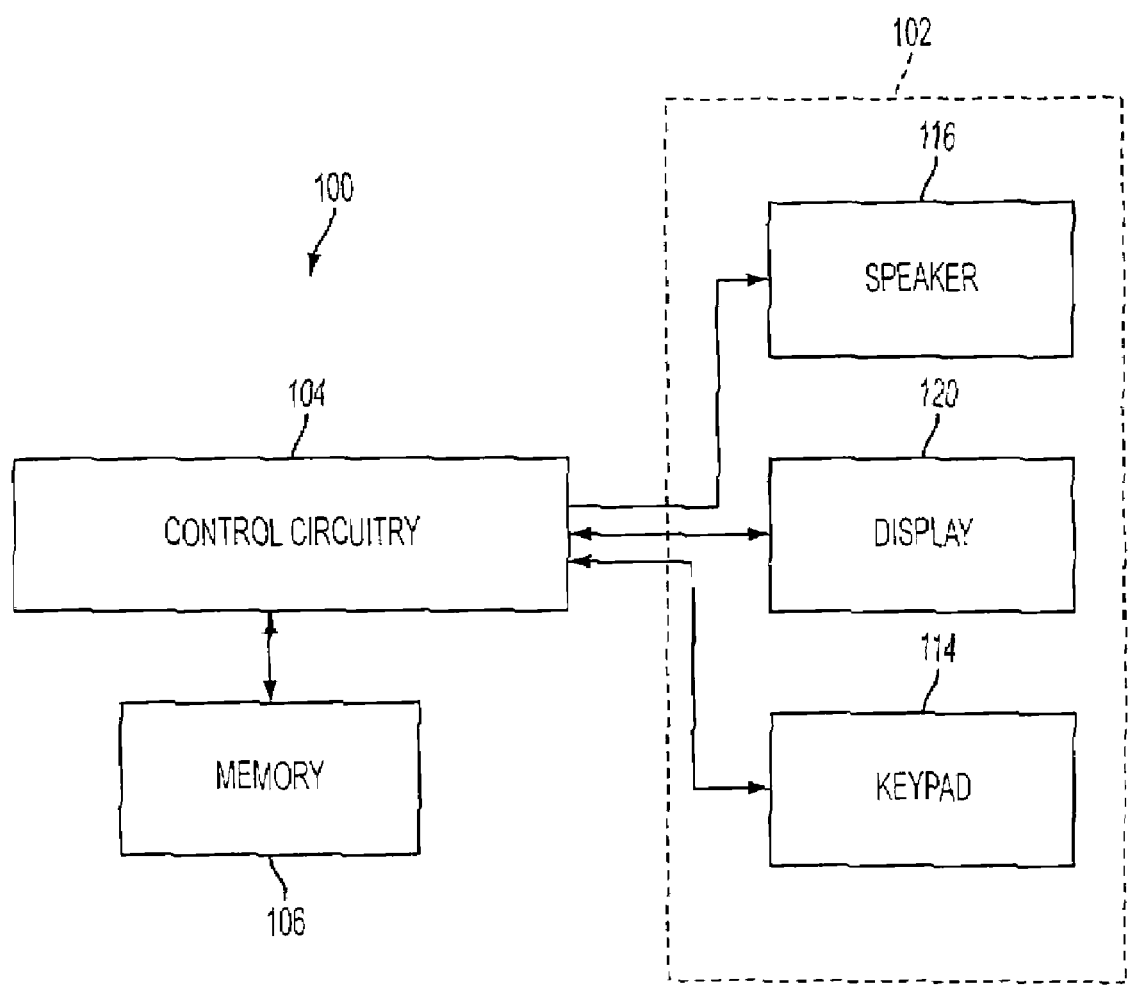
FIG. 10 is a schematic representation of a computing environment that can used to implement various aspects of the invention.

FIG. 10 illustrates a schematic diagram of a general computing environment that can be used to implement various aspects of the present invention. Various toothbrush arrangements may be described in the general context of computer-executable instructions, such as program modules, executed by one or more microprocessors or other devices. Generally, program modules include routines, programs, components, data structures, and the like that perform particular tasks or implement particular digital data types. In FIG. 10, a toothbrush 100 may include electronic components and application programs including a user interface 102, a control circuitry 104, and a memory 106. User interface 102 provides audio and/or visual signals to a user and enables a user to interact with the toothbrush electronic components. The user interface 102 is operatively connected to the control circuitry 104. The user interface 102 may optionally include a speaker device 116, a display device 120, and a keypad or button arrangement 114. The speaker device 116 provides audible signals to user. The display device 120 provides visual signals to the user in the form of alphanumeric characters, colors or graphical symbols. The display device 120 may be a device used for computing devices, such as a liquid crystal display (LCD). The control circuitry 104 may include a microprocessor (not shown) for use with digital data.

The control circuitry 104 is operatively coupled to memory 106. Memory 106 stores data installed or programmed by the user, including a game episode. Memory 106 may be any programmable type in which nonvolatile storage can be electrically erased and reprogrammed. Possible alternatives include flash memory, flash ROM, RAM with battery backup. It should be understood that a game episode formatted for toothbrush 100 may be downloaded to memory 106 or a game episode may be preload in the memory.

In one arrangement, memory 106 may be insertable in the control circuitry 104 so that various game programs can be interchangeably played with the same toothbrush. This embodiment memory 106 comprises a memory module with a housing, such as Compact Flash, Secure Digital Media and the like. The handle 10 may have a slot for receiving and retaining an insertable memory module. In this way, toothbrush 1 provides an oral care platform for expansion of games and other programming related to or associated with oral care. Nevertheless, the games could have entertaining value other than oral care.

The toothbrush 1 optionally can be provided with compartments and/or access panels for access to the various components, such as a power source. The power source can be, for example, a replaceable or rechargeable battery as well known.

The handle 10 may be designed to enable the user to easily grip and manipulate the toothbrush. More particularly, the handle 10 may be shaped and/or include ergonomic features to provide a higher degree of control for the user while maintaining comfort. Examples of ergonomic features include an overmolded grip portion that can be segmented and ergonomically sized for users. The handle 10 may include sections that are angled relative to each other and/or which are wider or narrower than other portions of the handle to provide increased control and comfort during use. In the embodiment shown in FIGS. 8A and 8B, for example, a textured grip portion 31 can be provided to provide a non-slip surface for the user to grip the toothbrush. The grip portion 31 can be provided on the same side of the handle 10 as the bristles 16, on the opposite side of the handle 10 as the bristles 16, or around the circumference of the handle 10 as shown in FIGS. 8A and 8B. As shown in FIG. 8B, an elastomeric portion 31 also may be included on the side of the head 12 opposite the bristles 16, e.g., for aesthetic purposes or the like.

The head 12, bristles 16, and any other tooth cleaning components of the toothbrush 1 can be ergonomically sized and shaped to facilitate tooth cleaning, including interproximal tooth cleaning. The head 12 can be generally elliptical or rectangular in shape, for example, although other configurations are contemplated. The bristles 16 generally extend from the surface of head 12 and can be of conventional size and spacing for effective tooth cleaning. A pick (not shown) optionally can be included and may have a size and conical shape adapted to promote interproximal cleaning effectiveness.

The head 12 may be integral with or permanently attached to the handle 10, or may be replaceable. One or more other oral surface engaging elements, such as a flossing element, plaque scrapper, elastomeric massaging elements, and the like, may also be present on the toothbrush 1. In practice, the toothbrush can have these any of these features alone or in any combination with other features not illustrated herein. It will also be appreciated that while the cleaning elements are illustrated herein as tufts of bristles 16, other cleaning elements of varying size, shape, cross-section and material may be used.

The toothbrush may have concave molded portions for holding and dispensing fragrance, flavorants, actives or other materials. For example, a plurality of sockets (not illustrated) may be located at one or both ends of the handle 10. The sockets can be sized and shaped to releasably hold fragrance, flavor-yielding capsules, or other materials to be dispersed. For example, sockets can be molded from elastomeric material as concave hemispheres of suitable dimensions to enable flavor-yielding capsules to be easily dispensed and replaced. Alternatively, the sockets can be configured to hold commercially available fragrance or flavor yielding gel capsules.

The head may be rigid or flexible. An example of a toothbrush having a flexible head is found in U.S. Pat. No. 6,442,787, which is incorporated by reference. The toothbrush has first and second sections with an elastomer section (or joint) located therebetween. Other details of flexible toothbrush heads, as well as examples of other flexible head configurations which can be used, are described in US 2006/0117508 A1, the disclosure of which is hereby incorporated by reference.

The handle and head sections can be molded from a plastic or resin such as polypropylene. Grip portions 31, buttons 20, 22, 30A, 30B, 30C, etc. and various other components of the toothbrush can be formed from elastomer materials well known to persons skilled in the art, such as propylene-ethylene copolymer elastomers. Elastomers can be used to form, for example, a handle or a portion thereof, a flexible joint in the head, a flexible pick, elastomeric cleaning elements, bristles, a tongue scraping element, other components of an oral care implement, or any combination thereof. The elastomers can be incorporated using conventional molding techniques well known to those of ordinary skill, such as overmolding or co-injection molding techniques.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention and described and claimed herein. While specific toothbrush configurations have been illustrated, the present invention is not limited to any of the aesthetic aspects shown and, in practice, may differ significantly from the illustrated configurations.

We claim:

1. A toothbrush comprising:
   a body comprising a handle and a head having tooth cleaning elements, the handle comprising:
   an input device;
   a computer implemented game executable on a processor having computer executable instructions for receiving a user input from the input device;
   a display displaying the game, the game comprising images of a plurality of oral care regions of a mouth;
   the processor causing the display to sequentially illuminate one of the plurality of oral care regions for each of a plurality of prescribed brushing intervals, each of the illuminated regions representing a portion of the mouth to be brushed during the brushing interval, and to subsequently display the game at a conclusion of the brushing intervals;
   the input device configured to enable a user to interact with the images while playing the game; and
   wherein the user interaction comprises manipulating the images.

2. The toothbrush of claim 1, further comprising a plurality of lighted areas isolated from and positioned outside of the display.

3. The toothbrush of claim 2, wherein the lighted areas are grouped in sections corresponding to brushing zones, and wherein the processor causes the lighted areas in one of the sections to be illuminated during a first prescribed brushing interval.

4. The toothbrush of claim 3, wherein the processor causes the lighted areas in each of the sections to be illuminated successively for respective prescribed brushing intervals.

5. The toothbrush of claim 1, wherein the computer implemented game graphically simulates removing plaque from teeth.

6. The toothbrush of claim 1, wherein the computer implemented game simulates trapping plaque between a set of upper and lower teeth.

7. A toothbrush, comprising:
 a body comprising a handle and a head having tooth cleaning elements, the handle comprising:
  a display displaying graphical objects of a plurality of segments shaped to resemble teeth or different sections of teeth, the segments collectively resembling a mouth;
  a processor which causes the display to sequentially illuminate one of the plurality of segments for each of a plurality of prescribed brushing intervals, each of the illuminated segments representing a portion of the mouth to be brushed during the brushing interval, and to subsequently display a game at a conclusion of the brushing intervals, the game including images of oral care regions of a mouth shown on the display; and
  an input device enabling a user to interact with the game to manipulate the images.

8. The toothbrush of claim 7, wherein the game graphically simulates removing plaque from teeth.

9. The toothbrush of claim 7, wherein the handle further comprises a plurality of sections each having a plurality of lighted areas isolated from and positioned outside of the display.

10. The toothbrush of claim 9, wherein the processor causes the lighted areas to illuminate after the conclusion of the prescribed brushing intervals.

11. The toothbrush of claim 1, wherein the images further comprise a plurality of segments shaped to resemble teeth or different sections of teeth.

* * * * *